US005602032A

United States Patent [19]
Liu et al.

[11] Patent Number: 5,602,032
[45] Date of Patent: Feb. 11, 1997

[54] *BACILLUS THURINGIENSIS* MUTANTS WHICH PRODUCE HIGH YIELDS OF CRYSTAL DELTA-ENDOTOXIN

[75] Inventors: Chi-Li Liu; Pamela G. Marrone; Jewel M. Payne, all of Davis, Calif.; Hanne Gurtler, Holte; Annette S. Petersen, Birkerød, both of Denmark

[73] Assignee: Abbott Laboratories, Abbott Park, Ill.

[21] Appl. No.: 377,888

[22] Filed: Jan. 25, 1995

Related U.S. Application Data

[63] Continuation-in-part of Ser. No. 182,904, Jan. 14, 1994, abandoned, which is a continuation of Ser. No. 906,038, Jun. 26, 1992, Pat. No. 5,279,962, which is a continuation of Ser. No. 613,337, Nov. 14, 1990, abandoned.

[30] Foreign Application Priority Data

Nov. 17, 1989 [DK] Denmark ................................ 5805/89
Dec. 12, 1989 [DK] Denmark ................................ 6274/89

[51] Int. Cl.$^6$ .................................................. C12N 1/20
[52] U.S. Cl. .................................. 435/252.31; 424/93.2; 424/93.461; 424/DIG. 8; 435/832
[58] Field of Search ........................... 435/252.31, 252.1, 435/832; 424/93.2, 93.461, DIG. 8

[56] References Cited

U.S. PATENT DOCUMENTS

| 4,766,203 | 8/1988 | Krieg et al. ................ 530/370 |
| 4,990,332 | 2/1991 | Payne et al. ................. 424/93 |
| 5,279,962 | 1/1994 | Gurtler et al. .............. 435/252.5 |

OTHER PUBLICATIONS

Wakisaka et al., Applied & Environ. Microbiol., 43(6): 1498–1500 (Jun. 1982).
Hofte et al, Microbiological Reviews, 53(2): 242–255 (1989).
Johnson et al, Applied & Environ. Microbiol., 42(2): 385–387 (1981).
Krieg et al, Journal of Applied Entomology, 96:500–508 (1983).
Hernstadt et al., Bio/Technology, 4:305–308 (1986).
C. C. Payne et al; British Crop Protection Conference–Pests & Diseases, pp. 231–238 (1984).
Nishiitsutsuji–Uwo et al, J. Invert. Pathol., 25:355–361 (1975).
Johnson et al, Can. J. Microbiol., 26:486–491 (1980).

*Primary Examiner*—John W. Rollins
*Attorney, Agent, or Firm*—Cheryl H. Agris; Michael J. Ward

[57] ABSTRACT

The invention relates to a mutant of *Bacillus thuringiensis* which produces a larger amount of crystal delta-endotoxin with a greater pesticidal activity as compared to the corresponding parental strain. The mutant may also have a larger crystal size as compared to the corresponding parental strain. The crystal delta-endotoxin produced by the mutant *Bacillus thuringiensis* will have an activity directed towards the same pest(s) as its parental *Bacillus thuringiensis* crystal delta-endotoxin. The invention further relates to a method for producing such a mutant, compositions comprising such a mutant as well as methods for controlling a pest(s) using these compositions.

18 Claims, No Drawings

BACILLUS THURINGIENSIS MUTANTS WHICH PRODUCE HIGH YIELDS OF CRYSTAL DELTA-ENDOTOXIN

This application is a continuation-in-part of application Ser. No. 08/182,904, filed Jan. 14, 1994, now abandoned which is a continuation of application Ser. No. 07/906,038, filed Jun. 26, 1992, now U.S. Pat. No. 5,279,962 which is a continuation of application Ser. No. 07/613,337, filed Nov. 14, 1990, now abandoned, incorporated herein by reference.

1. FIELD OF THE INVENTION

The invention relates to a mutant of *Bacillus thuringiensis* which produces a larger amount of crystal delta-endotoxin with a greater pesticidal activity as compared to the corresponding parental strain. The mutant may also have a larger crystal size as compared to the corresponding parental strain. The crystal delta-endotoxin produced by the mutant *Bacillus thuringiensis* will have an activity directed towards the same pest(s) as its parental *Bacillus thuringiensis* crystal delta-endotoxin. The invention further relates to a method for producing such a mutant, compositions comprising such a mutant as well as methods for controlling a pest(s) using these compositions.

2. BACKGROUND OF THE INVENTION

Every year, pests detrimental to agriculture, forestry, and public health cause losses in the millions dollars. Various strategies have been used control such pests.

One strategy is the use of chemical pesticides with a broad range or spectrum of activity. However, there are a number of disadvantages to using such chemical pesticides. Specifically, because of their broad spectrum of activity, these pesticides may destroy non-target organisms such as beneficial insects and parasites of destructive pests. Additionally, chemical pesticides are frequently toxic to animals and humans. Furthermore, targeted pests frequently develop resistance when repeatedly exposed to such substances.

Another strategy has involved the use of biopesticides, which make use of naturally occurring pathogens to control insect, fungal and weed infestations of crops. An example of a biopesticide is a bacterium which produces a substance toxic to the infesting pest. A biopesticide is generally less harmful to non-target organisms and the environment as a whole than chemical pesticides.

The most widely used biopesticide is *Bacillus thuringiensis*. *Bacillus thuringiensis* is a motile, rod-shaped, gram-positive bacterium that is widely distributed in nature, especially in soil and insect-rich environments. During sporulation, *Bacillus thuringiensis* produces a parasporal crystal inclusion(s) which is insecticidal upon ingestion to susceptible insect larvae of the order Lepidoptera, Diptera, or Coleoptera. The inclusion(s) may vary in shape, number, and composition. They are comprised of one or more proteins called crystal delta-endotoxins, which may range in size from 27–140 kDa. The insecticidal crystal delta-endotoxins are generally converted by proteases in the larval gut into smaller (truncated) toxic polypeptides, causing midgut destruction, and ultimately, death of the insect (Höfte and Whiteley, 1989, *Microbiol. Rev.* 53:242–255).

There are several *Bacillus thuringiensis* strains that are widely used as biopesticides in the forestry, agricultural, and public health areas. *Bacillus thuringiensis* subsp. *kurstaki* and *Bacillus thuringiensis* subsp. *aizawai* have been found to produce crystal delta-endotoxins specific for Lepidoptera. *Bacillus thuringiensis* subsp. *israelensis* has been found to produce crystal delta-endotoxins specific for Diptera (Goldberg, 1979, U.S. Pat. No. 4,166,112). *Bacillus thuringiensis* subsp. *tenebrionis* (Krieg et al., 1988, U.S. Pat. No. 4,766,203), has been found to produce a crystal delta-endotoxin specific for Coleoptera. Several *Bacillus thuringiensis* crystal delta-endotoxin proteins are also reportedly pesticidal to nematodes, Acari, Hymenoptera, Phthiraptera, Platyhelminthes, Homoptera, Blattodea, and Protozoa.

The isolation of another coleopteran toxic *Bacillus thuringiensis* strain was reported in 1986 (Herrnstadt et al., 1986, *Bio/Technology* 4:305–308; Herrnstadt and Soares, 1988, U.S. Pat. No. 4,764,372). This strain, designated "*Bacillus thuringiensis* subsp. *san diego*", M-7, has been deposited at the Northern Regional Research Laboratory, USA under accession number NRRL B-15939. However, the assignee of the '372 patent, Mycogen, Corp. has publicly acknowledged that *Bacillus thuringiensis* subsp. *san diego* is *Bacillus thuringiensis* subsp. *tenebrionis*. Furthermore, the '372 patent has been assigned to Novo Nordisk A/S. A spo$^+$cry$^-$ (asporogenous crystal forming) mutant of M-7 has purportedly been obtained by culturing M-7 in the presence of ethidium bromide (Herrnstadt and Gaertner, 1987, EP Application No. 228,228). However, there was no indication of increased production of delta-endotoxin, increased parasporal crystal size, and/or increased pesticidal activity relative to the parental, M-7 strain.

The delta-endotoxins are encoded by cry (crystal protein) genes. The cry genes have been divided into six classes and several subclasses based on relative amino acid homology and pesticidal specificity. The six major classes are Lepidoptera-specific (cryI), Lepidoptera- and Diptera-specific (cryII), Coleoptera-specific (cryIII), Diptera-specific (cryIV) (Höfte and Whiteley, 1989, *Microbiol. Rev.* 53:242–255), Coleoptera- and Lepidoptera-specific (referred to as cryV genes by Tailor et al., 1992, *Mol. Microbiol.* 6:1211–1217); and Nematode-specific (referred to as cryV and cryVI genes by Feitelson et al., 1992, *Bio/Technology* 10:271–275).

The utility of *Bacillus thuringiensis* strains for the control of pests is dependent upon efficient and economical production of the active toxins. This in turn is dependent upon the amount of crystal delta-endotoxins which can be produced by fermentation of the active *Bacillus thuringiensis* strains.

Consequently a recognized need for products of improved strength exists.

One way to fulfill this need would be to concentrate the preparations. However, this would add considerably to the production cost in comparison to the savings obtained in storage and transportation.

A much more elegant solution would be to create mutants of existing B.t. strains which produce substantially larger amounts of delta-endotoxin and have a substantially higher amount of pesticidal activity compared to its parental strain. Such mutants would give a more efficient and economical production of active delta-endotoxins and a possibility for manufacture of B.t. products with increased potency at equal or lower cost. This in turn would be an advantage for the user as reduced volumes of pesticide formulation have to be stored and handled for a given acreage. In addition, the users will have less container material to dispose of, thereby reducing the impact on the environment.

3. SUMMARY OF THE INVENTION

The invention is directed to a mutant that produces larger amounts of crystal delta-endotoxin than the corresponding parental strain, preferably more than about 1.25 times and most preferably more than about 1.5 times the amount with greater pesticidal activity and has activity directed towards the same pest as a corresponding parental strain.

As defined herein, a "parental strain" is the original Bacillus thuringiensis strain before mutagenesis. In a specific embodiment, the parental strain is a wild-type strain.

"Greater Pesticidal activity" as defined herein means at least 1.25 times and preferably more than about 1.5 more activity against a pest, times through killing or stunting of the growth of the pest, than the corresponding parental strain. In a preferred embodiment, the pesticidal activity of the mutant is between about 1.5 to about 5 times greater than the pesticidal activity of the corresponding parental Bacillus thuringiensis strain.

In a specific embodiment, the mutant may also have a larger crystal volume, preferably more than 1.25 times and most preferably more than twice the volume than the corresponding parental strain. The volume may be determined by photographing spore/crystal preparations using a microscope with a camera attachment. Measurements of the crystals in millimeters may be made, and then normalized to the average length of the spores in each photo to account for any differences in photo enlargement. The volume for the bipyramidal crystals is calculated using the following formula: $V=(width^2 \times length)/3$. Additionally, the mutants may have a sporulation frequency of at least 2 logs lower than the sporulation frequency of the parental strain.

The invention further relates to a method for obtaining the mutants of the present invention. The invention also relates to a pesticidal composition comprising such a mutant or spore thereof and a pesticidally acceptable carrier as well as methods for controlling a pest using such a composition.

4. DETAILED DESCRIPTION OF THE INVENTION

The mutants of the present invention may have activity against an insect pest (e.g., lepidopteran, coleopteran, dipteran), as well as snails, mites, or nematodes. The parental Bacillus thuringiensis may be a wild-type strain which includes but is not limited to Bacillus thuringiensis subsp. kurstaki, Bacillus thuringiensis subsp. aizawai, Bacillus thuringiensis subsp. galleriae, Bacillus thuringiensis subsp. entomocidus, Bacillus thuringiensis subsp. tenebrionis, Bacillus thuringiensis subsp. thuringiensis, Bacillus thuringiensis subsp. alesti, Bacillus thuringiensis subsp. canadiensis, Bacillus thuringiensis subsp. darmstadiensis, Bacillus thuringiensis subsp. dendrolimus, Bacillus thuringiensis subsp. finitimus, Bacillus thuringiensis subsp. kenyae, Bacillus thuringiensis subsp. morrisoni, Bacillus thuringiensis subsp. subtoxicus, Bacillus thuringiensis subsp. toumanoffi, Bacillus thuringiensis subsp. toumanoffi, Bacillus thuringiensis subsp. pondicheriensis, Bacillus thuringiensis subsp. shandogiensis, Bacillus thuringiensis subsp. sotto, Bacillus thuringiensis subsp. nigeriae, Bacillus thuringiensis subsp. yunnanensis, Bacillus thuringiensis subsp. dakota, Bacillus thuringiensis subsp. nidiana, Bacillus thuringiensis subsp. tohokuensis, Bacillus thuringiensis subsp. kumamotoensis, Bacillus thuringiensis subsp. tochigiensis, Bacillus thuringiensis subsp. thompsoni, Bacillus thuringiensis subsp. wuhanensis, Bacillus thuringiensis subsp. kyushuensis, Bacillus thuringiensis subsp. ostriniae, Bacillus thuringiensis subsp. tolworthi, Bacillus thuringiensis subsp. pakistani, Bacillus thuringiensis subsp. japonensis, Bacillus thuringiensis subsp. colmeri, Bacillus thuringiensis subsp. pondicheriensis, Bacillus thuringiensis subsp. shandongiensis, Bacillus thuringiensis subsp. neoleonensis, Bacillus thuringiensis subsp. coreanensis, Bacillus thuringiensis subsp. silo, Bacillus thuringiensis subsp. mexcanensis, and Bacillus thuringiensis subsp. israelensis.

In a specific embodiment, the parental Bacillus thuringiensis strain is Bacillus thuringiensis subsp. aizawai. In a most specific embodiment, the mutant has the identifying characteristics of EMCC0125, deposited with the NRRL and having the accession number NRRL B-21389.

In another embodiment, the parental strain may solely produce a CryIA(a)-like crystal delta-endotoxin. Such strains are disclosed in application Ser. No. 08/157,363, filed Nov. 23, 1993, incorporated herein by reference. The CryIA(a)-like crystal delta-endotoxin is encoded by at least one copy Of a cryIA(a)-like gene. As defined herein, a "cryIA (a)-like gene" is a DNA sequence encoding a CryIA(a)-like protein defined above. In a specific embodiment, the cryIA(a)-like gene has at least 90% homology to the cryIA(a) gene, preferably at least 95% homology to the cryIA(a) gene and most preferably at least 99% homology to the cryIA(a) gene and is shown in the sequence listing as SEQ ID NO:1 shown below.

```
CCTGGGTCAAAAATTGATATTTAGTAAAATTAGTTGCACTTTGTGCATTTTTTCATAAGA
TGAGTCATATGTTTTAAATTGTAGTAATGAAAAACAGTATTATATCATAATGAATTGGTA
TCTTAATAAAAGAGATGGAGGTAACTTATGGATAACAATCCGAACATCAATGAATGCATT
CCTTATAATTGTTTAAGTAACCCTGAAGTAGAAGTATTAGGTGGAGAAAGAATAGAAACT
GGTTACACCCCAATCGATATTTCCTTGTCGCTAACGCAATTTCTTTTGAGTGAATTTGTT
CCCGGTGCTGGATTTGTGTTAGGACTAGTTGATATAATATGGGGAATTTTTGGTCCCTCT
CAATGGGACGCATTTCTTGTACAAATTGAACAGTTAAATTAACCAAAGAATAGAAGAATT
CGCTAGGAACCAAGCCATTTCTAGATTAGAAGGACTAAGCAATCTTTATCAAATTTACGC
AGAATCTTTTAGAGAGTGGGAAGCAGATCCTACTAATCCAGCATTAAGAGAAGAGATGCG
TAATCAATTCAATGACATGAACAGTGCCCTTACAACCGCTATTCCTCTTTTGGCAGTTCA
AAATTATCAAGTTCCTCTTTTATCAGTATATGTTCAAGCTGCAAATTTACATTTATCAGT
TTTGAGAGATGTTTCAGTGTTTGGACAAAGGTGGGGATTTGATGCCGCGACTATCAATAG
TCGTTATAATGATTTAACTAGGCTTATTGGCAACTATACAGATTATGCTGTGCGCTGGTA
CAATACGGGATTAGAGCGTGTATGGGGACCGGATTCTAGAGATTGGGTAAGGTATAATCA
ATTTAGAAGAGAGCTAACACTTACTGTATTAGATATCGTTGCTCTATTCTCAAATTATGA
TAGTCGAAGGTATCCAATTCGAACAGTTTCCCAATTAACAAGAGAAATTTATACGAACCC
AGTATTAGAAAATTTTGATGGTAGTTTTCGTGGAATGGCTCAGAGAATAGAACAGAATAT
TAGGCAACCACATCTTATGGATATCCTTAATAGTATAACCATTTATACTGATGTGCATAG
AGGCTTTAATTATTGGTCAGGGCATCAAATAACAGCTTCTCCTGTAGGGTTTTCAGGACC
AGAATTCGCATTCCCTTTATTTGGGAATGCGGGGAATGCAGCTCCACCCGTACTTGTCTC
ATTAACTGGTTTGGGGATTTTTAGAACATTATCTTCACCTTTATATAGAAGAATTATACT
TGGTTCAGGCCCAAATAATCAGGAACTGTTTGTCCTTGATGGAACGGAGTTTTCTTTTGC
CTCCCTAACGACCAACTTGCCTTCCACTATATATAGACAAAGGGGTACAGTCGATTCACT
```

-continued

```
AGATGTAATACCGCCACAGGATAATAGTGTACCACCTCGTGCGGGATTTAGCCATCGATT
GAGTCATGTTACAATGCTGAGCCAAGCAGCTGGAGCAGTTTACACCTTGAGAGCTCCAAC
GTTTTCTTGGCAGCATCGCAGTGCTGAATTTAATAATATAATTCCTTCATCACAAATTAC
ACAAATACCTTTAACAAAATCTACTAATCTTGGCTCTGGAACTTCTGTCGTTAAAGGACC
AGGATTTACAGGAGGAGATATTCTTCGAAGAACTTCACCTGGCCAGATTTCAACCTTAAG
AGTAAATATTACTGCACCATTATCACAAAGATATCGGGTAAGAATTCGCTACGCTTCTAC
TACAAATTTACAATTCCATACATCAATTGACGGAAGACCTATTAATCAGGGTAATTTTTC
AGCAACTATGAGTAGTGGGAGTAATTTACAGTCCGGAAGCTTTAGGACTGTAGGTTTTAC
TACTCCGTTTAACTTTTCAAATGGATCAAGTGTATTTACGTTAAGTGCTCATGTCTTCAA
TTCAGGCAATGAAGTTTATATAGATCGAATTGAATTTGTTCCGGCAGAAGTAACCTTTGA
GGCAGAATATGATTTAGAAAGAGCACAAAAGGCGGTGAATGAGCTGTTTACTTCTTCCAA
TCAAATCGGGTTAAAAACAGATGTGACGGATTATCATATTGATCAAGTATCCAATTTAGT
TGAGTGTTTATCAGATGAATTTTGTCTGGATGAAAAACAAGAATTGTCCGAGAAAGTCAA
ACATGCGAAGCGACTTAGTGATGAGCGGAATTTACTTCAAGATCCAAACTTCAGAGGGAT
CAATAGACAACTAGACCGTGGCTGGAGAGGAAGTACGGATATTACCATCCAAGGAGGCGA
TGACGTATTCAAAGAGAATTACGTTACGCTATTGGGTACCTTTGATGAGTGCTATCCAAC
GTATTTATATCAAAAAATAGATGAGTCGAAATTAAAAGCCTATACCCGTTATCAATTAAG
AGGGTATATCGAAGATAGTCAAGACTTAGAAATCTATTTAATTCGCTACAATGCAAAACA
TGAAACAGTAAATGTGCCAGGTACGGGTTCCTTATGGCCGCTTTCAGCCCAAAGTCCAAT
CGGAAAGTGTGGAGAGCCGAATCGATGCGCGCCACACCTTGAATGGAATCCTGACTTAGA
TTGTTCGTGTAGGGATGGAGAAAAGTGTGCCCATCATTCGCATCATTTCTCCTTAGACAT
TGATGTAGGATGTACAGACTTAAATGAGGACCTAGGTGTATGGGTGATCTTTAAGATTAA
GACGCAAGATGGGCACGCAAGACTAGGGAATCTAGAGTTTCTCGAAGAGAAACCATTAGT
AGGAGAAGCGCTAGCTCGTGTGAAAAGAGCGGAGAAAAAATGGAGAGACAAACGTGAAAA
ATTGGAATGGGAAACAAATATCGTTTATAAAGAGGCAAAAGAATCTGTAGATGCTTTATT
TGTAAACTCTCAATATGATCAATTACAAGCGGATACGAATATTGCCATGATTCATGCGGC
AGATAAACGTGTTCATAGCATTCGAGAAGCTTATCTGCCTGAGCTGTCTGTGATTCCGGG
TGTCAATGCGGCTATTTTTGAAGAATTAGAAGGGCGTATTTTCACTGCATTCTCCCTATA
TGATGCGAGAAATGTCATTAAAAATGGTGATTTTAATAATGGCTTATCCTGCTGGAACGT
GAAAGGGCATGTAGATGTAGAAGAACAAAACAACCAACGTTCGGTCCTTGTTGTTCCGG
AATGGGAAGCAGAAGTGTCACAAGAAGTTCGTGTCTGTCCGGGTCGTGGCTATATCCTTC
GTGTCACAGCGTACAAGGAGGGATATGGAGAAGGTTGCGTAACCATTCATGAGATCGAGA
ACAATACAGACGAACTGAAGTTTAGCAACTGCGTAGAAGAGGAAATCTATCCAAATAACA
CGGTAACGTGTAATGATTATACTGTAAATCAAGAAGAATACGGAGGTGCGTACACTTCTC
GTAATCGAGGATATAACGAAGCTCCTTCCGTACCAGCTGATTATGCGTCAGTCTATGAAG
AAAAATCGTATACAGATGGACGAAGAGAGAATCCTTGTGAATTTAACAGAGGGTATAGGG
ATTACACGCCACTACCAGTTGGTTATGTGACAAAAGAATTAGAATACTTCCCAGAAACCG
ATAAGGTATGGATTGAGATTGGAGAAACGGAAGGAACATTTATCGTGGACAGCGTGGAAT
TACTCCTTATGGAGGAATAGTCTCATGCAAACTCAGGTTTAAATATCGTTTTCAAATCAA
TTGTCCAAGAGCAGCATTACAAATAGATAAGTAATTTGTTGTAATGAAAAACGGACATCA
CCTCCATTGAAACGGAGTGATGTCCGTTTTACTATGTTATTTTCTAGT
```

In a specific embodiment, the parental strain may be the B.t. strain EMCC0073 or EMCC0074 also disclosed in application Ser. No. 08/157,363. In a most specific embodiment, the mutant may have the identifying characteristics of EMCC0123, deposited with the NRRL and having the accession number NRRL B-21387 and the mutant or the identifying characteristics of EMCC0124 and having the accession number NRRL B-21388.

4.1. Methods of Obtaining the Mutant

The parental strain may be treated with a mutagen to induce a transposition event. Due to the nature of transposition, such mutagenesis will also cause a gene duplication, in this case, duplication of the cry gene. Specifically, in one method of mutating *Bacillus thuringiensis* strains and selecting such mutants that are capable of producing substantially larger amounts of crystal delta-endotoxins than their parental strains, the parental strain is:

i) treated with a mutagen, ii) the treated cells are cultured in a selective culture medium (e.g., NSMP medium); and iii) cells are selected which have a larger crystal size.

In step (i), the mutagen for example may be a chemical mutagen N-methyl-N'-nitro-N-nitrosoguanidine or ethyl methanesulfonate, gamma irradiation, X-ray or UV-irradiation.

The cells are selected visually by examining the cultured cells under a microscope. Cells which appear to have a larger crystal size are thus selected and delta-endotoxin production and activity is assayed.

In one embodiment, the following procedure is used after treating cells with mutagen:

i) growing mutagenized cells on a medium suitable for the selection of asporogenous and/or oligosporogenous strains, ii) selecting translucent colonies and growing the selected cells in a medium that does not fluidize on heating, and iii) deselecting truly asporogenous strains by subjecting the colonies to a heat treatment.

After deselection, the thus selected colonies are grown in a normal production medium, and a final selection for strains capable of increasing the crystal delta-endotoxin production is performed.

In step (i), a suitable medium could be a modified nutrient sporulation medium including phosphate (NSMP medium) as described by Johnson et al., In "Spores VI": eds. P. Gerhardt et al., pp. 248–254, 1975.

In step (iii) of the method of the invention, a suitable medium could be a NSMP medium supplemented with MgCl$_2$ and Gelrite.

Another method of obtaining the high producing mutants of the invention may be contemplated such as growing the parent strain in a liquid medium and selecting spontaneous mutants after spreading the culture broth on an agar medium suitable for selection of asporogenous and/or oligosporogenous mutants.

Other methods of screening for the high producing mutants of the invention may be contemplated such as separating the mutants from other material on the basis of mass directly through centrifugation or other means of separating for mass.

4.2. Compositions

The mutant *Bacillus thuringiensis* strains, crystal delta-endotoxins and/or spores of the invention, can be formulated into a pesticidal composition(s), that is for example, a suspension, a dispersion, an aqueous emulsion, a dusting powder, a dispersible powder, an emulsifiable concentrate, an aerosol or micro or macroencapulated granules or any other formulation that gives controlled release of *Bacillus thuringiensis*. Such compositions may be obtained by the addition of a surface active agent, e.g., a dispersing agent, emulsifying agent or wetting agent, or an inert carrier or other component to facilitate handling and application for particular target pests.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkylbenzene sulphonates or lower alkylnaphthalene sulphonates, e.g., butyl-naphthalene sulphonate; salts or sulphonated naphthalene-formaldehyde condensates or salts of polyacrylic acid; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g., the sodium sulphonate or dioctyl succinate. Non-ionic agents include condensation products of fatty acid esters, fatty alcohols, fatty acid amides or fatty- alkyl- or alkenyl-substituted phenols with ethylene oxide and/or propylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include inorganic minerals such as phyllosilicates, carbonates, sulfates, phosphates; organic materials such as sugar, starches, or cyclodextrins; or botanical materials such as powdered corncobs, rice hulls, walnut shells, cornmeal, pelleted grains, and cellulosic fibers.

The compositions of the present invention can be in a suitable form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition contains 0.1% to 99%, preferably 0.1% to 95% of the mutant, mutant or variant of the present invention, 1 to 98% of a solid or liquid inert carrier, and 0 to 50%, preferably 0.1% to 50% of a surfactant. These compositions will be administered at about 0.01 lb–5.0 lb per acre when in dry form and at about 0.01 pt–10 pts per acre when in liquid form.

In a further embodiment, the mutants of the present invention can be treated prior to formulation to prolong the pesticidal activity when the cells are applied to the environment of a target pest. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; histological fixatives, such as Bouin's fixative and Helly's fixative (see, for example, Humason, *Animal Tissue Techniques*, W. H. Freeman and Co., 1967); preservatives; UV sunscreens; spray adjuvants (humectants); antifoams; and stickers.

The compositions of the invention can be applied directly to the plant by, for example, spraying or dusting at the time when the pest has begun to appear on the plant or before the appearance of pests as a protective measure. Plants o be protected within the scope of the present invention include, but are not limited to, cereals (wheat, barley, rye, oats, rice, sorghum and related crops), beet (sugar beet and fodder beet), drupes, pomes and soft fruit (apples, pears, plums, peaches, almonds, cherries, strawberries, raspberries, and blackberries, tomatoes), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit/oranges, lemons, grapefruit, mandarins), vegetables (spinach, lettuce, asparagus, cabbages and other brassicae, carrots, onions, potatoes, paprika), lauraceae (avocados, cinnamon, camphor), deciduous trees and conifers (linden-trees, yew-trees, oak-trees, alders, poplars, birch-trees, firs, larches, pines), or plants such as maize, tobacco, nuts, coffee, sugar cane, tea, vines hops, bananas and natural rubber plants, as well as ornamentals. The preferred mode of application is by foliar spraying. It is generally important to obtain good control of pests in the early stages of plant growth as this is the time when the plant can be most severely damaged. The spray or dust can conveniently contain another insecticide or pesticide, e.g., fungicide, grass herbicide or fertilizer, if this is thought necessary. In a preferred embodiment, the composition of the invention is applied directly to the plant.

The compositions of the present invention may be effective against pests off the order Lepidoptera, e.g., *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis,* Archips sp., Argyroytaenia sp., *Athetis rainclara, Bombyx mori, Bucculatrix thurberiella, Cadra cautella,* Choristoneura sp., *Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupocoellia ambiguella, Eupoecilia ambiguellat Euproctis chrysorrhoea, Euxoa messoria, Galleria mellonella, Grapholita molesca, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugu-* brosa, Leucoma salicis, Lobesia botrana, Loxostege sticticalis, Lymantria dispar, Macalla thyrsisalis, Malacosoma sp., Mamestra brassicae, Mamestra configurata, Manduca quinquemaculata, Manduca sexta, Maruca testulalis, Melanchra picta, Operophtera brumata, Orgyia sp., Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera sp., Syngrapha falcifera, Thaurnstopoea pityocampa, Tineola bisselliella, Trichoplusia ni, Udea rubigalis, Xylomyges curialis, Yponomeuta madella;. The compositions of the invention may also be effective against insect pests of the order Coleoptera, e.g., Leptinotarsa sp., Acanthoscelides obtectus, Callosobruchus chinensis, Epilachna varivestis, pyrrhalta luteola, Cylas formicarius elegantulus, Listronotus oregonensis, Sitophilus sp., Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum, Tribolius destructor, Diptera, e.g., Aedes sp., Andes vittatus, Anastrepha ludens, Anastrepha suspensa, Anopheles barberi, Anopheles quadrimaculatus, Armigeres subalbatus, Calliphora sygian, Calliphora vicina, Ceratitis capitata, Chironomus tentans, Chrysomya rufifacies, Cochliomyia macellaria, Culex sp., Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsi tans morsi tans, Glossina morsi tans sub-morsi tans, Glossina pallidipes, Glossina palpalis gambiensis, Slossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica, Neobellieria sp., Nephrotoma suturalis, Ophyra aenescens, Phaenicla sericata, Phlebotomus sp., Phormia regina, Sabethes cyaneus, Sarcophaga bullata, Scatophaga stercorarla, Stomaxys calcitrans, Toxorhynchites amboinensis, Tripteroides bambusa; Acari, e.g., Oligonychus pratensis, Panonychus ulmi, Tetranychus urticae; Hymenoptera, e.g., Iridomyrmex humilis, Solenopsis invicta; Isoptera, e.g., Reticulitermes hesperus, Reticulitermes flavipes, Coptotermes formosanus, Zootermopsis angusticollis, Neotermes connexus, Incisitermes minor, Incisitermes immigrans; Siphonaptera, e.g., Ceratophyllus gallinae, Ceratophyllus niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis, Tunga panetrans; and Tylenchida, e.g., Melodidogyne incognita, Pratylenchus penestrans.

The following examples are presented by way of illustration, not by way of limitation.

5. EXAMPLES

5.1. Example 1

A mutant of B. thuringiensis subsp. tenebrionis with more than a twofold increase in crystal delta-endotoxin production has been isolated. Phase contrast microscopy, scanning electron microscopy and transmission electron microscopy of this mutant indicate that the high productivity of this mutant is due to changes in the regulation of crystal delta-endotoxin production relative to sporulation resulting in the production of protein crystals which are up to more than five times bigger than the crystals produced by the known coleopteran active Bacillus thuringiensis strains. The close correlation between crystal formation and sporulation seems to have been removed and the mutant produces high amounts of crystal delta-endotoxin prior to sporulation.

5.1.1. Production of High Yield Mutant

Spores of B. thuringiensis subsp. tenebrionis, strain DSM 5526 are gamma-irradiated to give a dosage of 7 kGy. The irradiated spores are spread onto NSMP agar plates (modified nutrient sporulation medium including phosphate as described by Johnson et al., In "Spores VI": ads. P. Gerhardt et al., pp. 248–254, 1975), a medium suitable for selection of asporogenous and/or oligosporogenous mutants.

The NSMP-agar plates are incubated at 30° C. for 2–3 days. Translucent colonies are picked out and transferred to NSMP gelrite plates (NSMP medium supplemented with $MgCl_2$ (0.57 g/l) and Gelrite, Kalco (20 g/l)).

The NSMP gelrite plates are incubated for one hour at 90° C. and then further incubated for 1–2 days at 30° C. Mutants that grew well on the NSMP gelrite plates are selected. In this way, all asporogenous mutants are deselected as they fail to grow after the heat treatment.

The selected mutants are grown in shakeflasks containing a commercial medium. The amounts of crystal delta-endotoxin produced are determined by immunological methods described below. Only mutants producing significantly higher amounts of crystal delta-endotoxin than the parent strain are selected.

The morphology of the selected mutants on solid medium and in liquid media are studied by phase contrast microscopy (×2500) and by scanning and transmission electron microscopy. The number of spores and crystals are counted and the size of the protein crystals are determined. Among the mutants obtained, one (DSM 5480) is selected for its outstanding ability to produce crystal delta-endotoxin.

The amount of crystal delta-endotoxin produced by mutant DSM 5480 is compared with that of DSM 2803 the original isolate of Bacillus thuringiensis subsp. tenebrionis, Bacillus thuringiensis subsp. tenebrionis, strain DSM 5526, Bacillus thuringiensis subsp. tenebrionis, strain NB178, isolated from Sandoz' Bacillus thuringiensis tenebrionis product TRIDENT® from 1989, strain NB 198, isolated from Sandoz' B. thuringiensis subsp. tenebrionis product TRIDENT® from 1990, "Bacillus thuringiensis subsp. san diego", strain NRRL-B-15939, and strain NB 197 isolated from Mycogen's B. thuringiensis subsp. san diego" product M-ONE® from 1990. As shown in Table I of Example 2, the yield improved mutant of the invention produces 2–3.5 times as much crystal delta-endotoxin as the coleopteran active strains of Bacillus thuringiensis available today.

5.2. Example 2

In this example, the crystal delta-endotoxin yield of Bacillus thuringiensis subspecies tenebrionis, mutant DSM 5480 is compared with the crystal delta-endotoxin yields of Bacillus thuringiensis subspecies tenebrionis strains DSM 2803 (the original isolate of Bacillus thuringiensis subsp. tenebrionis), DSM 5526 (a production strain of Novo-Nordisk), and NB 178 and NB 198 (production strains of Sandoz), and *Bacillus thuringiensis* subsp. *san diego*, strain NRRL-B 15939 and NB 197 (production strains of Mycogen) in a commercial medium. Each of the strains is grown for 17 hours at 30° C. on agar slants of the following composition expressed as gram per liter of distilled water.

| Peptone, Difco | 5 g |
|---|---|
| Beef extract, Difco | 3 g |
| Agar, Difco | 20 g |
| pH | 7.0 |

5 ml of a suspension of cells from each strain are then transferred to 100 ml of production medium in 500 ml baffle-bottom Erlenmeyer flasks. The production medium consisted of the following components in the quantities indicated (expressed as grams per liter of tap water).

| Soy bean meal | 50 g |
|---|---|
| Hydrolyzed starch | 40 g |
| $KH_2PO_4$ | 1.77 g |
| $K_2HPO_4$ | 4.53 g |
| pH | 7.0 |

The inoculated flasks are incubated at 30° C. with shaking (250 rpm). After 96 hours of incubation the culture broths are assayed for crystal delta-endotoxin yields by immunological methods.

The amounts of crystal delta-endotoxin produced by the individual strains are determined by rocket immunoelectrophoresis (RIE) and a photometric immunoassay (PIA) using antibodies raised against purified protein crystals from *Bacillus thuringiensis* subsp. *tenebrionis*.

400 mg of each culture broth are weighed. 7 ml trisodium phosphate buffer (0.125 M, pH 12) is added to each sample. The suspensions are shaken for 1 hour in order to solubilize the crystal delta-endotoxin proteins.

The samples are then centrifuged at 3,500 rpm for 15 minutes and the supernatants are tested for crystal delta-endotoxin by rocket immunoelectrophoresis against antiserum raised against purified protein crystals from *B. thuringiensis* subsp. *tenebrionis*. The amounts of crystal delta-endotoxin are determined relatively to a standard with known content of crystal protein.

The concentration of crystal delta-endotoxin is also determined by a photometric immunoassay. The crystal delta-endotoxins are dissolved in an alkaline solution. The dissolved proteins are precipitated by their antibodies. The rate of this reaction is determined turbidimetrically. The amounts of crystal delta-endotoxin are determined relatively to a standard with known content of crystal protein.

Crystal delta-endotoxins for production of the antibodies used in the assays are obtained from crystals isolated from *B. thuringiensis* subsp. *tenebrionis*. Polyclonal antibodies are raised by injecting rabbits subcutaneously every fortnight with 0.25 mg of crystal delta-endotoxin.

The results obtained are shown in the following Tables Ia and Ib. Crystal delta-endotoxin yields are expressed as BTTU/g (units per g culture broth, determined by rocket immunoelectrophoresis, RIE, or by a photometric immunoassay, PIA). The value used for pure *B. thuringiensis* subsp. *tenebrionis* crystal delta-endotoxin is 500,000 BTTU/g. The values indicated in Table Ia below being averages of 6–7 independent fermentations, and those in Table Ib being averages of 3 independent fermentations.

TABLE Ia

Crystal delta-endotoxin production by strains of *Bacillus thuringiensis* subsp. *tenebrionis* in shake flasks

| | Crystal delta-endotoxin yield | |
|---|---|---|
| Strain | RIE BTTU/g | PIA BTTU/g |
| DSM 2803 | 676 | 1293 |
| NRRL-B 15939 | 747 | 1126 |
| NB 178 | 986 | 1728 |
| DSM 5526 | 1097 | 1860 |
| DSM 5480 | 2382 | 4169 |

TABLE Ib

Crystal delta-endotoxin production by strains of *Bacillus thuringiensis* subsp. *tenebrionis* in shake flasks

| Strain | Crystal delta-endotoxin yield RIE BTTU/g |
|---|---|
| NB 197 | 1103 |
| NB 198 | 1237 |
| DSM 5480 | 2867 |

From Tables Ia and Ib, it appears that DSM 5480 produces more than three times as much crystal delta-endotoxin as the original strain of *Bacillus thuringiensis* subsp. *tenebrionis*, DSM 2803 and "*Bacillus thuringiensis* subsp. *san diego*", strain NRRL-B15939 and more than twice the amount of crystal delta-endotoxin as the strains used today for the manufacture of commercial products of *Bacillus thuringiensis* subsp. *tenebrionis*.

Phase contrast microscopy, scanning electron microscopy and transmission electron microscopy of *Bacillus thuringiensis* subsp. *tenebrionis*, mutant DSM 5480 have revealed that the protein crystals produced by this mutant are much bigger than the corresponding protein crystals produced by *Bacillus thuringiensis* subsp. *tenebrionis*, strains DSM 2803, DSM 5526, NB178 and NB 198, and "*Bacillus thuringiensis* subsp. *san diego*", strains NRRL-B 15939 and NB 197.

Culture broth of *Bacillus thuringiensis* subsp. *tenebrionis*, mutant DSM 5480 is tested for activity against *Leptinotarsa texana* larvae. The increased amount of crystal delta-endotoxin produced by mutant DSM 5480 as determined by the immunological methods is reflected in the biological activity against *Leptinotarsa texana* larvae.

5.3. Example 3

In this example, sporulation and parasporal crystal formation in *B. thuringiensis* subsp. *tenebrionis*, strains, DSM 2803, DSM 5526, NB 178 and NB 198, and mutant DSM 5480, and "*B. thuringiensis* subsp. *san diego*", strains NRRL-B 15939 and NB 197 are compared on solid medium and in liquid medium.

Each of the strains is grown for 2 days at 30° C. on agar plates of the following composition expressed as gram per liter of distilled water.

| Peptone, Difco | 5 g |
|---|---|
| Beef extract, Difco | 3 g |
| Agar, Difco | 20 g |
| pH | 7.0 |

Each of the strains is also grown in liquid medium. All strains are grown for 17 hours at 30° C. on agar slants. 5 ml of a suspension of cells from each strain are then transferred to 500 ml baffle bottom Erlenmeyer flasks each containing 100 ml of medium.

The medium consisted of the following components in the quantities indicated (expressed as grams per liter of tapwater).

| Liquid medium: | |
| --- | --- |
| Yeast extract | 5 g |
| Tryptone | 5 g |
| Glucose | 1 g |
| $KH_2PO_4$ | 0.8 g |
| pH | 7.0 |

The inoculated flasks are incubated at 30° C. with shaking (250 rpm) for 96 hours.

The morphology of the strains on the solid medium and in the liquid medium is studied daily by phase contrast microscopy (×2500). The number of spores and crystals are counted and the size of the parasporal crystals are determined. A few selected samples are also studied by scanning and transmission electron microscopy.

B. thuringiensis subsp. tenebrionis, strains DSM 2803, DSM 5526, NB 178 and NB 198, and "B. thuringiensis subsp. san diego", strains NRRL-B 15939 and NB 197 all sporulated well on both media. Before cell lysis, each cell contained a spore and a parasporal crystal. The size of the crystals is from 0.4 to 0.9–1.1 μm in length by the time of cell lysis, the average size of the protein crystals being 0.6–0.7 μm in length.

Mutant DSM 5480 produced only few spores (<$10^6$ spores/ml) on the solid medium and in the defined liquid medium. Before cell lysis most cells contained a huge protein crystal but no spore. The size of the protein crystals is from 0.4–0.7 μm to 5.0 μm, the average size of the protein crystals being 2.2–2.3 μm in length.

Ultrastructural analysis of cells from these media by transmission electron microscopy revealed that the sporulation process in the mutant had been started but had not been completed by the time of cell lysis. The sporulation process had reached different stages in the various cells. In cells where the sporulation had only reached stage II (forespore septum formation), the protein crystals filled up the entire cells.

In the production medium (Example 2) the mutant produced a higher number of spores ($10^7$–$10^8$ spores/ml). In this medium, the sporulation frequency of the mutant is 10–100 times lower than in the parent strain.

Thus, the mutant has retained its ability to produce normal spores. However, the sporulation frequency of the mutant seems to be strongly dependent on the media.

The size of the protein crystals produced by the individual strains are shown in Tables IIa and IIb.

TABLE IIa

Size of the protein crystals produced by coleopteran active B. thuringiensis strains available today.

| | Length of protein crystals in μm | | |
| --- | --- | --- | --- |
| Strain | Minimum value | Maximum value | Mean value |
| DSM 2803 | 0.4 | 0.9 | 0.7 |
| NRRL-B-15939 | 0.4 | 0.9 | 0.7 |

TABLE IIa-continued

Size of the protein crystals produced by coleopteran active B. thuringiensis strains available today.

| | Length of protein crystals in μm | | |
| --- | --- | --- | --- |
| Strain | Minimum value | Maximum value | Mean value |
| NB 178 | 0.5 | 0.9 | 0.7 |
| DSM 5526 | 0.4 | 0.9 | 0.7 |
| DSM 5480 | 0.7 | 5.0 | 2.3 |

TABLE IIb

Size of the protein crystals produced by coleopteran active B. thuringiensis strains available today.

| | Length of protein crystals in μm | | |
| --- | --- | --- | --- |
| Strain | Minimum value | Maximum value | Mean value |
| NB 197 | 0.4 | 0.7 | 0.6 |
| NB 198 | 0.4 | 1.1 | 0.7 |
| DSM 5480 | 0.4 | 4.2 | 2.0 |

From Tables IIa and IIb it is clear that mutant DSM 5480 produces much bigger protein crystals than other coleopteran active B.t. strains.

From the data obtained, it appears that the regulation of crystal delta-endotoxin production in relation to sporulation has been changed in the mutant. The mutant seems to produce the crystal delta-endotoxin prior to the development of spores hereby giving the cells a longer period for crystal delta-endotoxin production which result in the production of much bigger protein crystals by the time of cell lysis than in the parent strain. Depending on the available nutrients and the size of the crystal delta-endotoxins in the cells by the time of sporulation, a normal spore will be developed before the time of cell lysis.

5.4. Example 4

In this example, the high yielding Btt mutant DSM 5480 is used to produce high potency products for the control of Leptinotarsa texana larvae.

DSM 5480 is fermented on the production fermentation medium described in Example 2 in an aerated, stirred production fermentation tank. After 96 hours, the broth is recovered by centrifugation on a continuous centrifuge. The concentrated cream which contains the active protein crystals is stabilized by addition of microbial preservatives and pH is adjusted to 5.0. One portion of the concentrated cream is spray dried and later used for the formulation of wettable powder. The rest of the concentrated cream is used directly for formulation of two aqueous flowable concentrates (FC). The wettable powder is formulated as described in Table III. The formulation of the two FC's is described in Table IV.

TABLE III

NOVODOR ® wettable powder formulation

| Component | % by weight |
| --- | --- |
| Spray dried concentrated cream of Btt | 40 |
| Detergents | 9 |
| Anticaking agent | 1 |
| Inert filler | 50 |

TABLE IV

NOVODOR® FC formulations

| Component | NOVODOR® FC 1 % by weight | NOVODOR® FC 2 % by weight |
|---|---|---|
| Btt concentrated cream | 80 | 55 |
| Preservatives | 4 | 4 |
| Antifreeze agents | 9.1 | 19 |
| Detergents | 2.5 | 2.5 |
| pH regulator | 2.85 | 2.85 |
| water | 1.55 | 16.65 |
|  | 100.0 | 100.0 |

When using a value of 500,000 BTTU/g of pure crystal protein the content of active crystal protein in the formulations are:

|  |  | % Btt crystal protein |
|---|---|---|
| NOVODOR® WP | 70.8 KBTTU/g | 14.16 |
| NOVODOR® FC1 | 24.7 KBTTU/g | 4.94 |
| NOVODOR® FC2 | 14.2 KBTTU/g | 2.84 |

The detergents are chosen among the wide selection of suspension aids and wetting agents normally used in agricultural pesticide products. The anticaking agent is a hydrophilic silica and the inert filler is chosen from the generally used inert fillers such as bentonites, inorganic salts or clays. The preservatives used in the FC's are chosen from the group of food and cosmetic preservatives. The pH regulator is an inorganic acid.

5.5. Example 5

A field trial is conducted to prove the biological effect of the high yielding Btt mutant DSM 5480 on the main target pest, *Leptinotarsa texana* larvae. Yields are compared with those obtained from the two commercial products, Trident® and M-one®. The crop is potatoes.

The crop is sprayed 3 times on July 20th, July 27th and August 3rd (2nd generation larvae). The products and dosages used are:

|  | Product volume/acre | Potency KBTTU/g | % Btt crystal protein in the formulation |
|---|---|---|---|
| NOVODOR® FC 2 | 1 qt/acre | 14.2 | 2.84 |
|  | 1.5 qts/acre | 14.2 | 2.84 |
|  | 2.5 qts/acre | 14.2 | 2.84 |
|  | 3.0 qts/acre | 14.2 | 2.84 |
| TRIDENT® | 4 qts/acre | 5.5 | 1.10 |
| M-one® | 2 qts/acre | 8.9 | 1.78 |

The mean % control of CPB larvae compared to the untreated control is given in Table V. The *Leptinotarsa texana* pressure is very heavy in the untreated control: 370 larvae per 20 plants on August 1st and 904 larvae per 20 plants on August 8th.

TABLE V

|  |  | % control | |
|---|---|---|---|
| Treatment |  | August 1st | August 8th |
| NOVODOR® FC 2 | 1 qt | 99 | 99 |
| NOVODOR® FC 2 | 1.5 qts | 95 | 100 |
| NOVODOR® FC 2 | 2.5 qts | 98 | 99 |
| NOVODOR® FC 2 | 3 qts | 100 | 100 |
| TRIDENT® | 4 qts | 94 | 98 |
| M-one® | 2 qts | 98 | 98 |

These results clearly show that products made with the high yielding mutant DSM 5480 are effective for the control of colorado potato beetle larvae in the field. The crystal delta-endotoxin produced by the high yielding strain is fully active as 1.5 qts NOVODOR® FC give as good results as Trident at 4 qts and as good as M-one at 2 qts.

5.6. Example 6: Classical Mutagenesis of *Bacillus thuringiensis* CryIA(a) Strain EMCC0073

A lyophilized vial of a sporulated culture of *Bacillus thuringiensis* EMCC0073 is inoculated into a 250 ml baffled shake flask containing 50 ml nutrient broth in late afternoon and incubated for 12 hours at 30° C. with shaking at 250 rpm.

Volumes of 1.0 ml of the vegetative cells and 9.0 ml of 0.1 M phosphate buffer, pH 7 are injected into an "Isopac" vial containing 10 mg of N-methyl-N'-nitro-N-nitroso-guanidine (NTG, Sigma Product # M6263). The mixture is incubated at 30° C. for 5, 10, and 20 minutes with low speed shaking. At each time point, a 0.5 ml sample is removed, diluted, and plated onto Nutrient Broth agar plates. The resulting plates are incubated at 30° C. for 3 days or longer before colonies are selected for microscopic examination. Semi-translucent colonies are selected and are grown in the medium described in Example 7. Two morphologically different *Bacillus thuringiensis* mutants, EMCC0123 and EMCC0124, are selected for bioassay as described infra in Example 8.

5.7. Example 7: Cultivation of *Bacillus thuringiensis* EMCC0073 Mutants

Subcultures of *Bacillus thuringiensis* EMCC0073 and mutants thereof, EMCC0123 and EMCC0124, maintained on Nutrient Broth agar slants, are used to inoculate 250 ml baffled shake flasks containing 50 ml of medium with the following composition:

| Corn Steep Liquor | 15 g/l |
|---|---|
| Maltrin-100 | 40 g/l |
| Potato Starch | 30 g/l |
| $KH_2PO_4$ | 1.77 g/l |
| $K_2HPO_4$ | 4.53 g/l |

The pH of the medium is adjusted to 7.0 with 10 N NaOH.

After inoculation, the shake flasks are incubated at 30° C. on a rotary shaker at 250 rpm for 72 hours until sporulation and cell lysis releasing the crystals and spores are observed microscopically. The whole culture broths, obtained from the above fermentations, are used to characterize the insecticidal activity.

5.8. Example 8: Bioassay of Crystal Delta-Endotoxins from *Bacillus thuringiensis* Mutants EMCC0123 and EMCC0124 against *Spodoptera exigua* and *Heliothis zea*

Standard artificial diet composed of water, agar, sugar, casein, wheat germ, methyl paraben, sorbic acid, linseed oil, cellulose, salts, and vitamins is prepared by using methods known in the art. Whole broths from the *Bacillus thuringiensis* mutants EMCC0123 and EMCC0124 as described in Example 7 are diluted to 0.5 mg per ml and 1 mg per ml. A 0.7 ml aliquot of molten diet is poured into each well of a plastic tray bearing 40 individual wells and allowed to solidify. Aliquots of 50 μl of each diluted broth from the *Bacillus thuringiensis* mutants EMCC0123 and EMCC0124 are added to the surface of the diet and allowed to dry. Three to six eggs each of *Spodoptera exigua* and *Heliothis zea* are then applied to the surface of the solidified diet. The trays are covered with a perforated sheet of clear mylar and placed on racks and incubated for 7 days at 28° C. and 65% humidity.

After 7 days, insect stunting and mortality are rated. Each tray is given a sharp blow against a table top, and larvae that did not move are counted as dead. In the stunt scoring system, 4=full size larvae (control larvae), 3=¾ size of control larvae, 2=½ size of control larvae, 1=¼ size of control larvae, and 0=no growth. The smaller the stunt score, the higher the activity of the *Bacillus thuringiensis* whole broth preparation.

The results are shown in Table VI, infra. The insecticidal activities of the broths from the *Bacillus thuringiensis* mutants EMCC0123 and EMCC0124 are significantly greater than that of the parent strain *Bacillus thuringiensis* EMCC0073 against both *Heliothis zea* and *Spodoptera exigua*.

TABLE VI

Activity of *Bacillus thuringiensis* mutants EMCCO123 and EMCCO124 against *Heliothis zea* and *Spodoptera exigua*

| Sample | | *Spodoptera exigua* | | *Heliothis zea* | |
|---|---|---|---|---|---|
| | | % Mortality | Stunt Score | % Mortality | Stunt score |
| EMCC0123 | 1 mg | 100 | 0 | 83 | 0.2 |
| | 0.5 mg | 100 | 0 | 50 | 0.5 |
| EMCC0124 | 1 mg | 100 | 0.5 | 100 | 0.5 |
| | 0.5 mg | 100 | 0.5 | 38 | 1.4 |
| EMCC0073 | 1 mg | 75 | 0.2 | 33 | 1.2 |
| | 0.5 mg | 50 | 0.5 | 17 | 1.8 |

5.9. Example 9: Determination of Size of CryIA(a) crystals from *Bacillus thuringiensis* Mutants EMCC0123 and EMCC0124

Crystal measurements are made by photographing spore/crystal preparations with an Olympus BH2 microscope. Measurements of the crystals in millimeters are made with a ruler, and then normalized to the average length of the spores in each photo to account for any differences in photo enlargement. The volume for the bipyramidal crystals is calculated using the following formula: $V=(width^2 \times length)/3$. It is assumed that a mature endospore is approximately 1 μm in its longest diameter.

The results, shown in Table VII infra, indicate that the volumes of the crystals of *Bacillus thuringiensis* mutant EMCC0123 and *Bacillus thuringiensis* mutant EMCC0124 are more than 2.2 times and 2.0 times, respectively, the volume of the crystal of the parent strain *Bacillus thuringiensis* EMCC0073.

TABLE VII

Crystal dimensions of *Bacillus thuringiensis* EMCC0073 mutants

| Sample | Crystal Length (μm) | Range (μm) | Crystal Width (μm) | Range (μm) | Crystal Volume (μm$^3$) | Number Measured |
|---|---|---|---|---|---|---|
| EMCC0123 | 1.85 | 1.7–2.0 | 1.55 | 1.4–1.7 | 1.48 | 5 |
| EMCC0124 | 1.80 | 1.6–2.0 | 1.50 | 1.3–1.7 | 1.35 | 5 |
| EMCC0073 | 1.65 | 1.5–1.8 | 1.10 | 1.0–1.2 | 0.67 | 5 |

5.10. Example 10: Classical Mutagenesis of *Bacillus thuringiensis* subsp. *aizawai* Strain EMCC0087

A lyophilized vial of a sporulated culture of *Bacillus thuringiensis* subsp. *aizawai* EMCC0087 is inoculated into 50 ml of Nutrient Broth supplemented with 0.2% glucose in a 250 ml baffled shake flask and incubated overnight at 30° C. on a rotary shaker at 250 rpm. One ml of the overnight culture is inoculated into each of two 250 ml baffled shake flasks containing 50 ml of the same medium and incubated 3 additional hours. The whole broths of the two shake flasks are then combined. A 70 ml whole broth sample is centrifuged for 15 min at 12,000 rpm (Sorvall SS-34 rotor), and the pellet is resuspended in 10.5 ml of 0.1 M phosphate buffer, pH 7.

A volume of 10 ml of the cell suspension in 0.1 M phosphate buffer, pH 7 is injected into an "Isopac" vial containing 10 mg of N-methyl-N'-nitro-N-nitroso-guanidine (NTG, Sigma Product# M6263). After a 20 minute exposure time, a sample is removed, diluted, and plated on Nutrient Broth agar plates.

Plates are incubated at 30° C. for three days or longer before colonies are selected for microscopic examination. One *Bacillus thuringiensis* subsp. *aizawai* mutant, EMCC0125, is selected based on crystal size observed microscopically. The parent strain produces bipyramidal crystals, while the mutant produces large bipyramidals and cylinders as well as irregular shaped crystals.

Relative quantitation of toxin protein is done using SDS-PAGE, scanning the gel and using integrated peak densities to determine the amount of protein relative to the parent strain *Bacillus thuringiensis* subsp. *aizawai* EMCC0087. The *Bacillus thuringiensis* subsp. *aizawai* mutant EMCC0125 produced 1.6 times more toxin per cell than the parent strain *Bacillus thuringiensis* subsp. *aizawai* EMCC0087.

5.11. Example 11: Cultivation of *Bacillus thuringiensis* subsp. *aizawai* Mutant EMCC0125

A subculture of *Bacillus thuringiensis* subsp. *aizawai* mutant EMCC0125, maintained on a Nutrient Broth agar plate, is used to inoculate a 250 ml baffled shake flask containing 50 ml of the medium with the composition described in Example 7.

After inoculation, the shake flask is incubated at 30° C. on a rotary shaker at 250 rpm for 88 hours. The whole culture broth is used to characterize the insecticidal activity.

5.12. Example 12: Bioassay of Whole Broth from *Bacillus thuringiensis* subsp. *aizawai* Mutant EMCC0125 against *Spodoptera exigua*

The potency of the whole broth from *Bacillus thuringiensis* subsp. *aizawai* mutant EMCC0125 is determined by diet incorporation bioassay using third instar *Spodoptera exigua* larvae.

The *Bacillus thuringiensis* subsp. *aizawai* mutant EMCC0124 whole broth from Example 11 is serially diluted to establish the range of potency. The parent strain, *Bacillus thuringiensis* subsp. *aizawai* EMCC0087 cultivated as described in EXAMPLE 11, is also run.

Standard artificial diet composed of water, agar, sugar, casein, wheat germ, methyl paraben, sorbic acid, linseed oil, cellulose, salts, and vitamins is prepared by using methods known in the art. The *Bacillus thuringiensis* subsp. *aizawai* mutant EMCC0125 whole broth is serially diluted to give 16 ml aliquots. Each aliquot is added to 184 g of molten diet. The mixture is subsequently homogenized and then poured into a plastic tray bearing 40 individual wells. Once the diet had cooled and solidified, one third instar *Spodoptera exigua* larva is added to each well, and the trays are covered with a perforated sheet of clear mylar. The trays are placed on racks and incubated for four days at 28° C. and 65% humidity.

Per cent mortality is calculated after 5 days and the data is analyzed via parallel probit analysis. LC50 values, LC90 values, the slope of the regression lines, and coefficient of variation (CV) are determined. LC50 results are expressed in terms of colony forming units (cfu) to compensate for variation in growth rates of the cultures. Samples are bioassayed a minimum of 3 times.

The results are shown in Table VIII, infra. The potency of the *Bacillus thuringiensis* subsp. *aizawai* mutant EMCC0125 is approximately 1.8 times that of the parent strain *Bacillus thuringiensis* subsp. *aizawai* EMCC0087.

TABLE VIII

Potency of *Bacillus thuringiensis* subsp. aizawai mutant EMCC0125 on *Spodoptera exigua*

| Sample | LC50 | LC90 | Slope | CV |
|---|---|---|---|---|
| EMCC0087 | $1.7 \times 10^6$ | $6.3 \times 10^6$ | 2.2 | 17.1 |
| EMCC0125 | $9.5 \times 10^5$ | $3.5 \times 10^6$ | 2.6 | 13.6 |

6. DEPOSIT OF MICROORGANISMS

The following strains of *Bacillus thuringiensis* have been deposited in the Agricultural Research Service Patent Culture Collection (NRRL), Northern Regional Research Center, 1815 University Street, Peoria, Ill. 61604, USA.

| Strain | Accession Number | Deposit Date |
|---|---|---|
| EMCC0073 | NRRL B-21014 | November 16, 1992 |
| EMCC0087 | NRRL B-21147 | October 6, 1993 |
| EMCC0123 | NRRL B-21387 | January 18, 1995 |
| EMCC0124 | NRRL B-21388 | January 18, 1995 |
| EMCC0125 | NRRL B-21389 | January 18, 1995 |

The following strains of *Bacillus thuringiensis* have been deposited with the Deutsche Sammlung yon Mikroorganismen und Zellkulturen GmbH, Mascheroderweg 1b, D-3300 Braunschweig, Germany.

| Strain | Accession Number | Deposit Date |
|---|---|---|
| NB 176-1 | DSM 5480 | August 10, 1989 |
| NB 125 | DSM 5526 | September 14, 1989 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for controlling a pest comprising applying to the pest a pesticidally effective amount of a composition which comprises (a) a mutant of a parental *Bacillus thuringiensis* strain producing higher amounts of a crystal delta-endotoxin with a greater pesticidal activity than a corresponding parental strain wherein the crystal delta-endotoxin produced by the mutant *Bacillus thuringiensis* strain has a crystal volume which is at least about 1.5 times the crystal volume of said parental swain and an activity directed towards the same pest as a crystal delta-endotoxin produced by the parental *Bacillus thuringiensis* strain and (b) a pesticidally acceptable carrier.

2. The method according to claim 1 in which the mutant produces at least about 1.25 times as much crystal delta-endotoxin than the parental strain.

3. The method according to claim 1 in which the mutant produces at least about 1.5 times as much crystal delta-endotoxin than the parental strain.

4. The method according to claim 1 in which the pesticidal activity of the mutant is at least 1.25 times the amount of the parental strain.

5. The method according to claim 1 in which the pesticidal activity of the mutant is at least 1.5 times the amount of the parental strain.

6. The method according to claim 1 in which the crystal volume of said mutant is at least about twice the crystal volume of said parental strain.

7. The method according to claim 1 in which the pest is a lepidopteran pest.

8. The method according to claim 1 in which the mutant produces a CryI crystal delta-endotoxin.

9. The method according to claim 1 in which the mutant produces a CryIA(a)-like crystal delta-endotoxin.

10. The method according to claim 1 in which the mutant is a mutant of *Bacillus thuringiensis* EMCC0073.

11. The method according to claim 1 in which the mutant has the identifying characteristics of *Bacillus thuringiensis* EMCC0123, deposited with the NRRL, having an accession number of NRRL B-21387.

12. The method according to claim 1 in which the mutant has the identifying characteristics of *Bacillus thuringiensis*

EMCC0124, deposited with the NRRL, having an accession number of NRRL B-21388.

13. The method according to claim 1 in which the mutant is a mutant of *Bacillus thuringiensis* subsp. *aizawai*.

14. The method according to claim 1 in which the mutant has the identifying characteristics of *Bacillus thuringiensis* EMCC0125, deposited with the NRRL, having an accession number of NRRL B-21389.

15. The method according to claim 1 in which the parental strain is a wild-type strain.

16. The method according to claim 1 in which the mutant shows a sporulation frequency at least two logs lower than the sporulation frequency of the parental strain.

17. A method for controlling a pest comprising applying to the pest a pesticidally effective amount of a composition which comprises (a) a crystal delta-endotoxin obtained from a mutant of a parental *Bacillus thuringiensis* strain wherein the crystal delta-endotoxin has a crystal volume at least about 1.5 times a crystal volume of and a greater pesticidal activity towards the same pest than a crystal delta-endotoxin obtained from the parental *Bacillus thuringiensis* strain and (b) a pesticidally acceptable carrier.

18. The method according to claim 17 in which the composition further comprises a spore obtained from the mutant of the parental *Bacillus thuringiensis* strain.

* * * * *

UNITED STATES PATENT AND TRADEMARK OFFICE
CERTIFICATE OF CORRECTION

PATENT NO. : 5,602,032
DATED : February 11, 1997
INVENTOR(S) : Liu, et. Al.

It is certified that error appears in the above-indentified patent and that said Letters Patent is hereby corrected as shown below:

Column 20, line 35, change "swain" to --strain--.

Column 20, line 59, change "Cry1A" to --CryIA--.

Signed and Sealed this

Twenty-fourth Day of June, 1997

Attest:

BRUCE LEHMAN

*Attesting Officer*    *Commissioner of Patents and Trademarks*